United States Patent
Harling et al.

(10) Patent No.: US 6,762,192 B2
(45) Date of Patent: Jul. 13, 2004

(54) TETRAHYDRONAPHTHYRIDINYL-CARBOXAMIDES HAVING ANTI-CONVULSANT ACTIVITY

(75) Inventors: John David Harling, Sawbridgeworth (GB); Frank Peter Harrington, Sawbridgeworth (GB); Mervyn Thompson, Harlow (GB)

(73) Assignee: SmithKline Beechum p.l.c., Brentford (GB)

( * ) Notice: Subject to any disclaimer, the term of this patent is extended or adjusted under 35 U.S.C. 154(b) by 0 days.

(21) Appl. No.: 10/154,997

(22) Filed: May 23, 2002

(65) Prior Publication Data

US 2002/0143029 A1 Oct. 3, 2002

Related U.S. Application Data

(63) Continuation of application No. 09/719,335, filed as application No. PCT/GB99/01826 on Jun. 9, 1999, now Pat. No. 6,410,555.

(30) Foreign Application Priority Data

Jun. 12, 1998 (GB) .............................. 9812683

(51) Int. Cl.$^7$ .......................... A61K 31/44; C07D 47/04
(52) U.S. Cl. ........................ 514/300; 514/278; 546/18; 546/122; 546/81
(58) Field of Search ................ 546/18, 122; 514/278, 514/300

(56) References Cited

U.S. PATENT DOCUMENTS 6,245,778 B1 * 6/2001 Hadley et al. ............... 546/300
6,410,555 B1 * 6/2002 Harling et al. .............. 514/300

FOREIGN PATENT DOCUMENTS

| WO | WO 92/22293 | 12/1992 |
| WO | WO 97/48683 | 12/1997 |
| WO | WO 98/54184 | 12/1998 |

* cited by examiner

Primary Examiner—Bernard Dentz
(74) Attorney, Agent, or Firm—Linda E. Hall; Stephen Venetianer; Charles M. Kinzig

(57) ABSTRACT

Compounds of formula (I) and pharmaceutically acceptable salts and solvates:

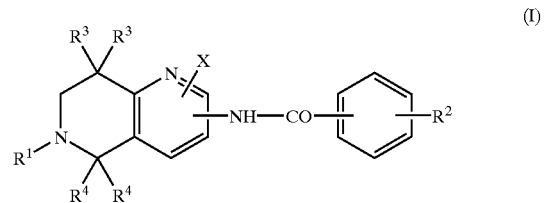

(I)

where $R^1$ is hydrogen, $C_{1-6}$ alkyl (optionally substituted by hydroxy or $C_{1-4}$alkoxy), phenyl-$C_{1-4}$alkyl-, $C_{1-6}$alkenyl, $C_{1-6}$alkynyl;

$R^2$ is hydrogen or up to three substituents selected from halogen, $NO_2$, CN, $N_3$, $CF_3O$—, $CF_3S$—, $CF_3CO$—, $C_{1-6}$alkyl, $C_{1-6}$alkenyl, $C_{1-6}$alkynyl, $C_{1-6}$perfluoroalkyl, $C_{3-6}$cycloalkyl, $C_{3-6}$cycloalkyl-$C_{1-4}$alkyl-, $C_{1-6}$alkylO—, $C_{1-6}$alkylCO—, $C_{3-6}$cycloalkylO—, $C_{3-6}$cycloalkylCO—, $C_{3-6}$cycloalkyl-$C_{1-4}$alkylO—, $C_{3-6}$cycloalkyl-$C_{1-4}$alkylCO—, phenyl, phenoxy, benzyloxy, benzoyl, phenyl-$C_{1-4}$alkyl-, $C_{1-6}$alkylS—, $C_{1-6}$alkylSO$_2$—, $(C_{1-4}$alkyl)$_2$NSO$_2$—, $(C_{1-4}$alkyl)NHSO$_2$—, $(C_{1-4}$alkyl)$_2$NCO—, $(C_{1-4}$alkyl)NHCO— or CONH$_2$;
or —NR$^5$R$^6$ where $R^5$ is hydrogen or $C_{1-4}$ alkyl, and $R^6$ is hydrogen, $C_{1-4}$alkyl, formyl, —CO$_2$C$_{1-4}$alkyl or —COC$_{1-4}$alkyl;
or two $R^2$ groups together form a carbocyclic ring that is saturated or unsaturated.

$R^3$ groups and $R^4$ groups are each independently hydrogen or $C_{1-6}$ alkyl and/or the two $R^3$ groups and/or the two $R^4$ groups together form a $C_{3-6}$ spiroalkyl group, provided that at least one $R^3$ or $R^4$ group is not hydrogen; and X is selected from hydrogen, halogen, cyano, alkyl and alkoxy, are useful in the treatment and prophylaxis of epilepsy, migraine, and other disorders.

6 Claims, No Drawings

TETRAHYDRONAPHTHYRIDINYL-CARBOXAMIDES HAVING ANTI-CONVULSANT ACTIVITY

This application is a continuation of Ser. No. 09/719,335 now U.S. Pat. No. 6,410,555, filed Feb. 16, 2001 which is a national stage entry of PCT/GB99/01826 filed Jun. 9, 1999.

This invention relates to novel compounds, to processes for preparing them, and to their use as therapeutic agents.

WO97/48683 (SmithKline Beecham) discloses that benzamide compounds of formula (A) below possess anti-convulsant activity and are therefore believed to be useful in the treatment and/or prevention of anxiety, mania, and related depression disorders.

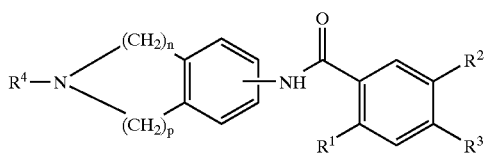

(A)

where n and p are independently integers from 1 to 4 and (n+p) is from 2 to 5;

$R^1$ is $C_{1-6}$alkylO—;

$R^2$ is hydrogen, halogen, CN, $N_3$, trifluoromethyldiazirinyl, $CF_3$, $CF_3O$—, $CF_3S$—, $CF_3CO$—, $C_{1-6}$alkyl, $C_{3-6}$cycloalkyl, $C_{3-6}$cycloalkyl-$C_{1-4}$alkyl-, $C_{1-6}$alkylO—, $C_{1-6}$alkylCO—, $C_{3-6}$cycloalkylCO—, $C_{3-6}$cycloalkyl-$C_{1-4}$alkylCO—, phenyl, phenoxy, benzyloxy, benzoyl, phenyl-$C_{1-4}$ alkyl-, $C_{1-6}$alkylS—, $C_{1-6}$alkylSO$_2$—, $(C_{1-4}$alkyl), NSO$_2$— or $(C_{1-4}$alkyl)NHSO$_2$—;

$R^3$ is hydrogen, halogen, $NO_2$, CN, $N_3$, trifluoromethyldiazirinyl, $C_{1-6}$ alkylO—, $C_{1-6}$ alkylS—, $C_{1-6}$ alkyl, $C_{3-6}$cycloalkyl, $C_{3-6}$cycloalkyl-$C_{1-4}$alkyl-, $C_{1-6}$alkenyl, $C_{1-6}$alkynyl, $CF_3$ CO—, $C_{1-6}$alkylCO—, $C_{3-6}$cycloalkylCO—, $C_{3-6}$cycloalkyl-$C_{1-4}$alkylCO—, phenyl, phenoxy, benzyloxy, benzoyl, phenyl-$C_{1-4}$alkyl-, or —NR$^5$R$^6$ where R$^5$ is hydrogen or $C_{1-4}$ alkyl, and R$^6$ is hydrogen, $C_{1-4}$alkyl, —CHO, —CO$_2$C$_{1-4}$alkyl or —COC$_{1-4}$alkyl;

$R^4$ is hydrogen, $C_{1-6}$ alkyl, $C_{1-6}$ alkenyl, or $C_{1-6}$ alkynyl.

It has now been surprisingly found that tetrahydronaphthyridinyl-carboxamide compounds of formula (I) below possess anti-convulsant activity and are therefore believed to be useful in the treatment and/or prevention of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia. Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, and amyotrophic lateral sclerosis (ALS).

Accordingly, the present invention provides a compound of formula (I):

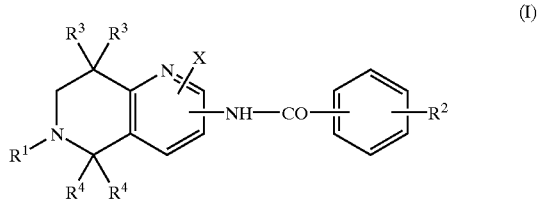

(I)

where $R^1$ is hydrogen, $C_{1-6}$alkyl (optionally substituted by hydroxy or $C_{1-4}$alkoxy), phenyl-$C_{1-4}$alkyl-, $C_{1-6}$alkenyl, or $C_{1-6}$alkynyl;

$R^2$ is hydrogen or up to three substituents selected from halogen, $NO_2$, CN, $N_3$, $CF_3O$—, $CF_3S$—, $CF_3SO_2$—, $CF_3CO$—, $C_{1-6}$alkyl, $C_{1-6}$alkenyl, $C_{1-6}$alkynyl, $C_{1-6}$perfluoroalkyl, $C_{3-6}$cycloalkyl, $C_{3-6}$cycloalkyl-$C_4$alkyl-, $C_{1-6}$alkylO—, $C_{1-6}$alkylCO—, $C_{3-6}$cycloalkylO—, $C_{3-6}$cycloalkylCO—, $C_{3-6}$cycloalkyl-$C_{1-4}$alkylO—, $C_{3-6}$cycloalkyl-$C_{1-4}$alkylCO—, phenyl, phenoxy, benzyloxy, benzoyl, phenyl-$C_{1-4}$alkyl-, $C_{1-6}$alkylS—, $C_{1-6}$alkylSO$_2$—) $(C_{1-4}$alkyl)$_2$NSO$_2$—, $(C_{1-4}$alkyl)NHSO$_2$—, $(C_{1-4}$alkyl)$_2$NCO—, $(C_{1-4}$alkyl)NHCO— or CONH;

or —NR$^5$R$^6$ where R) is hydrogen or $C_{1-4}$ alkyl, and R$^6$ is hydrogen, $C_{1-4}$alkyl, formyl, —COC$_{1-4}$alkyl or —COC$_{1-4}$alkyl;

or two $R^2$ groups together form a carbocyclic ring that is saturated or unsaturated, optionally interrupted by O or NH;

$R^3$ groups and $R^4$ groups are each independently hydrogen or $C_{1-6}$ alkyl and/or the two $R^3$ groups and/or the two $R^4$ groups together form a $C_{3-6}$ spiroalkyl group, provided that at least one $R^3$ or $R^4$ group is not hydrogen; and X is selected from hydrogen, halogen, cyano, alkyl and alkoxy.

The compounds of this invention are tetrahydronaphthyridinyl-carboxamides, especially (tetrahydronaphthyridin-3-yl)carboxamides. The carboxamide moiety is typically a benzamide, but when two $R^2$ groups form a carbocyclic ring, this is typically a 5–7 membered ring, and the carboxamide moiety may be a naphthalene carboxamide or an indane carboxamide, or when interrupted by O or NH may be a benzofuran carboxamide or an indole carboxamide.

In the formula (I), alkyl groups, including alkyl groups that are part of other moieties, such as alkoxy or acyl, may be straight chain or branched. Phenyl groups, including phenyl groups that are part of other moieties, in $R^2$ may optionally be substituted with one or more independently selected halogen or $C_{1-6}$ alkyl. $C_{1-6}$ alkoxy or $C_{1-6}$ alkyl-carbonyl.

Suitable $C_{3-6}$ cycloalkyl groups include cyclopropyl, cyclobutyl, cyclopentyl, and cyclohexyl. Suitable halo substituents include fluoro, chloro, iodo and bromo.

It should be appreciated that compounds of the present invention possess chiral centres and as such may exist in different enantiomeric forms, the present invention extends to each enantiomeric form and mixtures thereof including diastereoisomers and racemates.

Preferably, the two $R^3$ groups are the same, and the two $R^4$ groups are the same; typically either both $R^3$ groups are gem-dialkyl or spiro-alkyl, preferably gem-dialkyl, and both $R^4$ groups are hydrogen, or vice versa.

Accordingly one suitable group of compounds is of formula (IA):

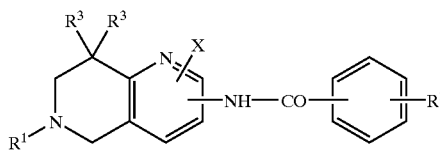

A further suitable group is of formula (IB):

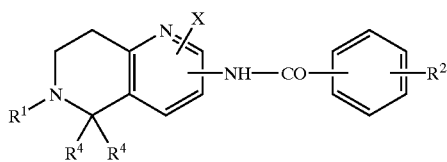

where $R^1$, $R^2$, $R^3$, $R^4$, X are as defined above.

A suitable group of compounds of formula (I) have
$R^1$ as hydrogen, methyl, ethyl, propyl, benzyl, hydroxyethyl, methoxyethyl,
$R^2$ as hydrogen or one or more of methyl, ethyl, n-butyl, iso-propyl, t-butyl, phenyl, methoxy, ethoxy, iso-propoxy, cyclopropylmethoxy, n-butoxy, phenoxy, benzyloxy, amino, acetylamino, nitro, azido, cyano, bromo, chloro, fluoro, iodo, acetyl, propionyl, pivaloyl, n-butyroyl, iso-butyroyl, benzoyl, iodobenzoyl, trifluoromethyl, perfluoroethyl, trifluoromethoxy, trifluoroacetyl, methanesulfonyl, n-propylsulfonyl, isopropylsulfonyl, dimethylsulfamoyl,
$R^3$ one or both is hydrogen or methyl,
$R^4$ one or both is hydrogen or methyl.

A preferred group of compounds of formula (I) have
$R^1$ as hydrogen, methyl,
$R^2$ as hydrogen or one or more of methyl, ethyl, i-propyl, t-butyl, methoxy, ethoxy, i-propoxy, bromo, chloro, cyano, trifluoromethyl,
$R^3$ both methyl,
$R^4$ both hydrogen.

Examples of compounds of formula (I) are:

N-(5,6,7,8-tetrahydro-6,8,8-trimethyl[1,6]naphthyridin-3-yl)benzamide;
N-(5,6,7,8-tetrahydro-6,8,8-trimethyl[1,6]naphthyridin-3-yl)-3-cyano-4-iso-propylbenzamide;
N-(5,6,7,8-tetrahydro-6,8,8-trimethyl[1,6]naphthyridin-3-yl)-4-methoxy-3-trifluoromethylbenzamide;
N-(5,6,7,8-tetrahydro-6,8,8-trimethyl[1,6]naphthyridin-3-yl)-3-bromo-4-ethylbenzamide;
N-(5,6,7,8-tetrahydro-6,8,8-trimethyl[1,6]naphthyridin-3-yl)-3-bromo-4-ethoxybenzamide;
N-(5,6,7,8-tetrahydro-6,8,8-trimethyl[1,6]naphthyridin-3-yl)-3-chloro-4-iso-propyloxybenzamide;
N-(5,6,7,8-tetrahydro-6,8,8-trimethyl [1,6]naphthyridin-3-yl)-3-bromo-4-iso-propyloxybenzamide;
N-(5,6,7,8-tetrahydro-6,8,8-trimethyl[1,6]naphthyridin-3-yl)-3-acetyl-4-iso-propyloxybenzamide;
N-(5,6,7,8-tetrahydro-6,8,8-trimethyl[1,6]naphthyridin-3-yl)-4-ethoxy-3-trifluoromethylbenzamide;
N-(8,8-dimethyl-5,6,7,8-tetrahydro[1,6]naphthyridin-3-yl)-4-methoxy-3-trifluoromethylbenzamide;
N-(5,6,7,8-tetrahydro-6,8,8-trimethyl[1,6]naphthyridin-3-yl)-3-bromo-4-methoxybenzamide;
N-(5,6,7,8-tetrahydro-6,8,8-trimethyl[1,6]naphthyridin-3-yl)-3-chloro-4-methoxybenzamide;
N-(5,6,7,8-tetrahydro-6,8,8-trimethyl[1,6]naphthyridin-3-yl)-3-cyano-4-methoxybenzamide;
N-(5,6,7,8-tetrahydro-6,8,8-trimethyl[1,6]naphthyridin-3-yl)-3-cyano-4-ethylbenzamide;
N-(5,6,7,8-tetrahydro-6,8,8-trimethyl[1,6]naphthyridin-3-yl)-3-bromo-4-methylbenzamide;
N-(5,6,7,8-tetrahydro-6,8,8-trimethyl[1,6]naphthyridin-3-yl)-3-pivaloylbenzamide;
N-(5,6,7,8-tetrahydro-6,8,8-trimethyl[1,6]naphthyridin-3-yl)-5-chloro-2-methoxy-4-iso-propyloxybenzamide;
N-(5,6,7,8-tetrahydro-6,8,8-trimethyl[1,6]naphthyridin-3-yl)-3-cyano-4-ethoxybenzamide;
N-(5,6,7,8-tetrahydro-6,8,8-trimethyl[1,6]naphthyridin-3-yl)-4-methoxy-3-trifluoroacetylbenzamide;
N-(5,6,7,8-tetrahydro-6,8,8-trimethyl[1,6]naphthyridin-3-yl)naphthalene-2-carboxamide;
N-(5,6,7,8-tetrahydro-6,8,8-trimethyl[1,6]naphthyridin-3-yl)-3-cyano-4-iso-propyloxybenzamide;
N-(5,6,7,8-tetrahydro-6,8,8-trimethyl[1,6]naphthyridin-3-yl)-3-acetyl-4-ethylbenzamide;
N-(5,6,7,8-tetrahydro-6,8,8-trimethyl[1,6]naphthyridin-3-yl)-2,3-dihydrobenzofuran-5-carboxamide;
N-(5,6,7,8-tetrahydro-6,8,8-trimethyl[1,6]naphthyridin-3-yl)-3-n-butyroyl-4-methoxybenzamide;
N-(5,6,7,8-tetrahydro-6,8,8-trimethyl[1,6]naphthyridin-3-yl)-4-methoxy-3-n-propionylbenzamide;
N-(5,6,7,8-tetrahydro-6,8,8-trimethyl[1,6]naphthyridin-3-yl-iso-butyroyl-4-methoxybenzamide;
N-(8,8-dimethyl-5,6,7,8-tetrahydro[1,6]naphthyridin-3-yl)-4-ethoxy-3-trifluoromethylbenzamide;
N-(8,8-dimethyl-5,6,7,8-tetrahydro[1,6]naphthyridin-3-yl)-3-acetyl-4-iso-propyloxybenzamide;
N-(8,8-dimethyl-5,6,7,8-tetrahydro[1,6]naphthyridin-3-yl)-3-bromo-4-methoxybenzamide;
N-(8,8-dimethyl-5,6,7,8-tetrahydro[1,6naphthyridin-3-yl)-3-chloro-4-methoxybenzamide;
N-(8,8-dimethyl-5,6,7,8-tetrahydro[1,6]naphthyridin-3-yl)-4-methoxy-3-pentafluoroethyl benzamide;
N-(8,8-dimethyl-5,6,7,8-tetrahydro(1,6]naphthyridin-3-yl)-4-iso-propoxy-3-trifluoromethyl benzamide;
N-(8,8-dimethyl-5,6,7,8-tetrahydro[1,6]naphthyridin-3-yl)-4-ethyl-3-trifluoromethyl benzamide;
N-(8,8-dimethyl-5,6,7,8-tetrahydro[1,6]naphthyridin-3-yl)-3-bromo-4-iso-propyl benzamide;
N-(5,6,7,8-tetrahydro-6,8,8-trimethyl[1,6]naphthyridin-3-yl)-3-chloro-4-ethoxybenzamide;
N-(5,6,7,8-tetrahydro-6,8,8-trimethyl[1,6]naphthyridin-3-yl)-3-fluoro-4-methoxybenzamide;
N-(5,6,7,8-tetrahydro-6,8,8-trimethyl[1,6]naphthyridin-3-yl)-4-methoxy-3-pentafluoroethylbenzamide;
N-(8,8-dimethyl-5,6,7,8-tetrahydro[1,6]naphthyridin-3-yl)-3-fluoro-4-methoxybenzamide;
N-(8,8-dimethyl-5,6,7,8-tetrahydro[1,6]naphthyridin-3-yl)-4-methoxy-3-propionylbenzamide, and;
N-(5,6,7,8-tetrahydro-6,8,8-trimethyl[1,6]naphthyridin-3-yl)-indole-2-carboxamide.

When synthesised, these compounds are often in salt form, such as the hydrochloride or trifluoroacetate, and such salts also form part of this invention. Such salts may be used in preparing pharmaceutically acceptable salts. The compounds and their salts may be obtained as solvates, such as hydrates, and these also form part of this invention.

The above compounds and pharmaceutically acceptable salts thereof, especially the hydrochloride, and pharmaceutically acceptable solvates, especially hydrates, form a preferred aspect of the present invention.

The administration of such compounds to a mammal may be by way of oral, parenteral, sub-lingual, nasal, rectal, topical or transdermal administration.

An amount effective to treat the disorders hereinbefore described depends on the usual factors such as the nature and severity of the disorders being treated and the weight of the mammal. However, a unit dose will normally contain 1 to 1000 mg, suitably 1 to 500 mg, for example an amount in the range of from 2 to 400 mg such as 2, 5, 10, 20, 30, 40, 50, 100, 200, 300 and 400 mg of the active compound. Unit doses will normally be administered once or more than once per day, for example 1, 2, 3, 4, 5 or 6 times a day, more usually 1 to 4 times a day, such that the total daily dose is normally in the range, for a 70 kg adult of 1 to 1000 mg, for example 1 to 500 mg, that is in the range of approximately 0.01 to 15 mg/kg/day, more usually 0.1 to 6 mg/kg/day, for example 1 to 6 mg/kg/day.

It is greatly preferred that the compound of formula (I) is administered in the form of a unit-dose composition, such as a unit dose oral, including sub-lingual, rectal, topical or parenteral (especially intravenous) composition.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disinterants, colorants, flavourings, and wetting agents. The tablets may be coated according to well known methods in the art. Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting, agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil oily esters such as esters of glycerine, propylene glycol, or ethyl alcohol; preservatives, for example methyl or propyl p-hydroxybenzoate or sorbic acid, and if desired conventional flavouring or colouring agents. Oral formulations also include conventional sustained release formulations, such as tablets or granules having an enteric coating.

For parenteral administration, fluid unit dose forms are prepared containing the compound and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

As is common practice, the compositions will usually be accompanied by written or printed directions for use in the medical treatment concerned.

Accordingly, the present invention further provides a pharmaceutical composition for use in the treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, and amyotrophic lateral sclerosis (ALS) which comprises a compound of formula (I), or a pharmaceutically acceptable salt or solvate thereof, and a pharmaceutically acceptable carrier.

The present invention also provides a method of treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, and amyotrophic lateral sclerosis (ALS) comprising administering to the sufferer in need thereof an effective or prophylactic amount of a compound of formula (I), or a pharmaceutically acceptable salt or solvate thereof.

In a further aspect the invention provides the use of a compound of formula (I), or a pharmaceutically acceptable salt or solvate thereof, for the manufacture of a medicament for the treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy. Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, and amyotrophic lateral sclerosis (ALS).

In a further aspect the invention provides the use of a compound of formula (I), or a pharmaceutically acceptable salt or solvate, thereof as a therapeutic agent, in particular for the treatment and/or prophylaxis of anxiety, mania, depression, panic disorders and/or aggression disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, and amyotrophic lateral sclerosis (ALS).

Another aspect of the invention is a process for the preparation of compounds of formula (I) as herein before described which comprises reacting a compound of formula (II)

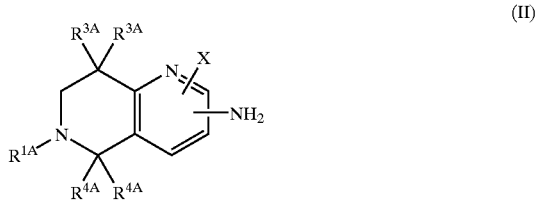

(II)

where $R^{1A}$, $R^{3A}$, and $R^{4A}$ are $R^1$, $R^3$, and $R^4$ as defined for formula (I) or a group or groups convertible to $R^1$, $R^3$, and $R^4$, and X is as defined for formula (I) with a compound of formula (III)

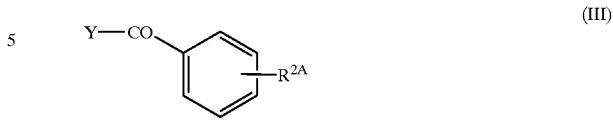

(III)

where Y is a leaving group such as Cl or OH, and $R^{2A}$ groups are independently $R^2$ as defined for formula (I) or a group or groups convertible to $R^2$, and where required converting an $R^{1A}$, $R^{2A}$, $R^{3A}$, $R^{4A}$ group to a $R^1$, $R^2$, $R^3$, $R^4$ group, converting one $R^1$, $R^2$, $R^3$, $R^4$, X group to another $R^1$, $R^2$, $R^3$, $R^4$, X group, or separating any enantiomers, or converting a salt product to the free base or another pharmaceutically acceptable salt, or converting a free base product to a pharmaceutically acceptable salt.

Conventional conditions for condensation of amines with carboxylic acids or active derivatives thereof, such as acid chlorides, may be used. For example the amides and acids may be reacted in the presence of a mixture of ethyl (dimethylaminopropyl)-carbodiimide/hydroxybenzotriazole in a suitable solvent such as dimethyl formamide, and amines and acid chlorides may be reacted together in a suitable solvent such as ethyl acetate or dichloromethane, optionally in the presence of a base such as triethylamine.

Conversions of an $R^{1A}$, $R^{2A}$, $R^{3A}$, $R^{4A}$ group to a $R^1$, $R^2$, $R^3$, $R^4$ group typically arise when a protecting group is needed during the above coupling reaction or during the preparation of the reactants by the procedures described below. Interconversion of one $R^1$, $R^2$, $R^3$, $R^4$. X group to another typically arises when one compound of formula (I) is used as the immediate precursor of another compound of formula (I) or when it is easier to introduce a more complex or reactive substituent at the end of a synthetic sequence.

Reaction of a compound of formula (III) which is an acid chloride (Y=Cl) typically results in formation of the hydrochloride salt of the compound of formula (I). Hydrochloride salts may also be obtained by passing HCl gas into a solution of the free base product, or adding a solution of HCl in ether.

Compounds of formula (II) may be prepared from a compound of formula (IV):

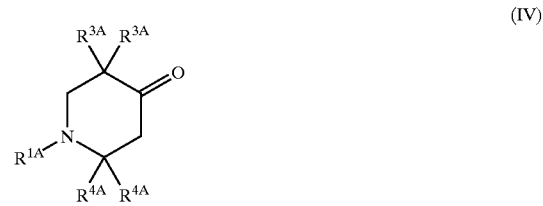

(IV)

by reaction with a dinitro-1-methylpyrid-2-one compound of formula (V):

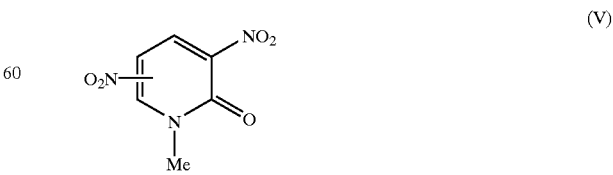

(V)

in a solution of ammonia in a suitable solvent such as methanol, to obtain a compound of formula (VI) using a procedure similar to that of S. Takada et al. J. Med. Chem, 1996, 39, 2844:

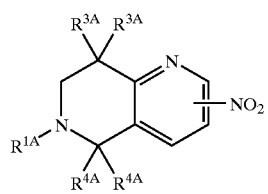

(VI)

Compounds of formula (VI) may be converted to compounds of formula (II) by hydrogenation or reduction of the nitro group. For example, a compound of formula (VI) may be hydrogenated by treatment with hydrogen in a suitable solvent such as methanol in the presence of a palladium/carbon catalyst. Alternatively, a compound of formula (VI) may be reduced with stannous chloride in concentrated hydrochloric acid in a suitable solvent such as ethanol.

Compounds of formula (IV) may be prepared using the procedures of Katyalyan et al., Bull. Acad. Sci. USSR (Engl) 1968, 2436.

Compounds of formula (V) may be prepared using the procedure of E. Matsumura. M. Ariga and Y. Tohda. Bull. Chem. Soc. Japan, 52 (8), 2413–2419,(1979).

Compounds of formula (III) may be prepared by further substitution of commercially available benzoic acid derivatives using conventional procedures, or by oxidation of corresponding substituted benzyl alcohols. Alternatively benzoic acids can be prepared from correpondingly substituted phenols, for example by formation of the acetate, coversion to an acetophenone and then to the desired acid.

Where the above described intermediates are novel compounds, they also form part of this invention.

The preparation of compounds of formula (II) is illustrated by the following Descriptions; the preparation of compounds of formula (III) is illustrated by the following Preparations and Procedures: the preparation of compounds of this invention is illustrated by the following Examples. The utility of compounds of this invention is shown by the Pharmacological Data that follow the Examples.

DESCRIPTION 1

1,3,3-Trimethylpiperidio-4-one

The title compound was prepared according to the procedure of Katyalyan et al. Bull. Acad. Sci. USSR (Engl) 1968, 2436, b.p 70° C. at 16 mm Hg; $^m/_z$ (API$^+$): 142.1 (MH+)

DESCRIPTION 2

3-Nitro-3,6,7,8-tetrahydro-6,8,8-trimethyl[1,6]naphthyridine 3,5-Dinitro-1-methylpyridin-2-one [prepared by the method of E. Matsumura. M. Ariga and Y. Tohda. Bull. Chem. Soc. Japan. 1979, 52, 2413–2419] (2g: 10 mmol) was suspended in MeOH (50 ml) and treated with 0.88 aq. ammonia (10 ml; 157 mmol), 1,3,3-Trimethylpiperidin-4-one (1.7 g; 12 mmol) was added and the mixture heated at 70° C. for 5 h. The mixture was cooled to room temperature then evaporated to dryness in vacuo. The residue was digested with dichloromethane (2×50 ml) and the hot solution decanted from the red gum. The extracts were combined, evaporated to dryness in vacuo and the residue purified by chromatography on SiO$_2$, with 50% ethyl acetate:60–80° C. petroleum to give the title compound as a yellow oil, which solidified on standing (1.05 g: 48%).

$^1$H NMR (250 MHz: CDCl$_3$) δ: 1.38 (6H, s), 2.47 (3H, s), 2.55 (2H, s), 3.64 (2H, s), 8.09 (1H, d, J=3 Hz), 9.25 (1H, d, J=3 Hz); $^m/_z$ (API$^+$): 222.1 (MH+)

DESCRIPTION 3

3-Amino-5,6,7,8-tetrahydro-6,8,8-trimethyl[1,6]naphthyridine

The product from Description 2 (930 mg; 4.20 mmol) was dissolved in MeOH (30 ml) and the mixture treated with 10% palladium on carbon (150 mg) then hydrogenated at STP until hydrogen uptake ceased. Catalyst was removed by filtration through Celite and the filtrate and washings combined and evaporated to dryness in vacuo. The residue was triturated under diethyl ether containing a little dichloromethane and the title compound collected by filtration washed with diethyl ether and dried in vacuo (795 mg: 84%).

$^1$H NMR (250 MHz: CD$_3$OD) δ$_H$: 1.73–1.99 (2H, m), 2.34–2.55 (5H, m), 2.63 (1H, d, J=17 Hz), 3.29 and 3.36 (1H, dd, J=17.5 Hz), 3.66–3.71 (1H, m), 3.99(1H, d, J=6 Hz), 6.95 (1H, d, J=3 Hz), 7.95 (1H, d, J=3 Hz): $^m/_z$ (API$^+$): 190.16 (MH

Preparation 1

3-Bromobenzyl TBMS ether

To a solution of 3-bromobenzyl alcohol (5.00 g, 0.027 mole) in dichloromethane (30 ml). Et$_3$N (4.2 ml, 0.03 mole) was added a 1 M solution tert-butyldimethylsilyl chloride in dichloromethane (28.0 ml) dropwise. The mixture was allowed to stir at room temperature overnight, then water (30 ml) was added. The organic layer was washed with brine, dried (Na$_2$SO$_4$) and evaporated to give a red oil which was purified by flash chromatography on silica gel using 20% ether in hexane to give a colouorless oil (8.0 g).

Preparation 2

3-Pivaloylbenzylalcohol TBDMS Ether n-Butyllithium (2.80 ml, 7.00 mmol. 2.5M in hexane) was slowly added to a solution of Preparation 1 TBDMS ether (1.80 g, 6.0 mmol) in dry THF (10 ml) over 5 min at −78° C. The reaction mixture was maintained under argon at −78° C. for 1 h, and N,O-dimethyl-hydroxy pivaloyl amide (0.86 g, 6.60 mmol) in THF (2 ml) was added dropwise with stirring at −78° C. The resulting mixture was allowed to stir at −78° C. for 2.5 h, quenched with NH$_4$Cl solution and allowed to warm to room temperature. The mixture was extracted with ether (2×50 ml), the combined organics were dried (Na$_2$SO$_4$) and concentrated in vacuo to give the title compound as a colourless oil (1.75 g $^m/_z$ (API+): 307 (MH$^+$; 8%).

Preparation 3

3-Pivaloylbenzylalcohol

The ether of Preparation 2 (1.470, 4.80 mmol) was dissolved in methanol (25 ml): conc. HCl (20 drops) was added and the whole allowed to stir at room temperature for 4 h. Saturated NaHCO$_3$ solution was added and the mixture extracted with ether (2×50 ml). The organic layer was dried over sodium sulfate and evaporation in vacuo save title compound as a colourless oil (0.80 g).

$^m/_z$ (API+): 193 (MH$^+$: 17%).

Preparation 4

3-Pivaloylbenzoic Acid

3-Pivaloylbenzyl alcohol (0.80 g, 4.16 mmol) was dissolved in dioxane (20 ml). A solution of KOH (0.35 g, 6.30 mmol) in water (5 ml) was added followed by $KMnO_4$ (1.45 g, 9.17 mmol). The mixture was stirred at room temperature over the weekend. The solution was filtered through Celite and extracted with ether. The aqueous phase was acidified with dil. HCl and extracted with ether (3×50 ml). The organic layer was dried over magnesium sulphate and concentrated in vacuo to afford the title compound as a white solid (0.80 g).

$^1$H NMR (250 MHz, $CDCl_3$)δ: 1.38 (9H, s), 7.55 (1H, t), 7.92 (1H, d, J=6.5 Hz), 8.20 (1H, d, J=6.5 Hz), 8.44 (1H, s).

Preparation 5

3-Trifluoroacetylbenzoic Acid

The title compound was prepared from diethyl trifluoroacetamide and 3-bromobenzyl TBDMS ether using a method similar to that described in Preparations 1, 2, 3 and 4.

$m/z$ (API−): 217 (M−H$^+$: 20%).

Preparation 6

Methyl 3-Chloro-4-iso-propoxybenzoate

Methyl 3-chloro-4-hydroxybenzoate (5 g, 26.8 mmol) in DMF (45 ml) was treated with potassium carbonate (7.41 g, 53.6 mmol), 2-iodopropane (3.85 ml. 40.2 mmol) and then stirred at 25° C. for 18 h. Work-up with ethyl acetate (save the title compound (6.1 g).

Preparation 7

3-Chloro-4-iso-propoxybenzoic acid

Methyl 3-chloro-4-iso-propoxybenzoate (5.5 g, 24.1 mmol) was hydrolysed using 1M NaOH (36 ml) in methanol (80 ml). Extraction and work-up with ethyl acetate gave the title compound (4.3 g).

$^1$H NMR (DMSO-$D_6$) δ: 1.33 (6H, d), 4.79 (1H, m), 7.24 (1H, d), 7.87 (2H, m)

Preparation 8

3-Bromo-4-ethoxybenzoic Acid

The title compound was prepared from 4-ethylbenzoic acid in a manner similar to that of Procedure 1.

$^1$H NMR (DMSO-$D_6$) δ: 1.45 (3H, t, J=7 Hz), 4.26(2H, q, J=7 Hz), 7.26 (1H, d, J=9 Hz), 7.98(1H, d, J=2.9 Hz), 8.12(1H, d, J=2 Hz)

Preparation 9

3-Bromo-4-ethylbenzoic Acid

The title compound was prepared from 4-ethylbenzoic acid in a manner similar to that of Procedure 1.

$^1$H NMR (DMSO-$D_6$) δ: 1.20 (3H, t, J=7 Hz), 2.78 (2H, q, J=7 Hz), 7.50 (1H, d, J=8 Hz), 7.90(1H, dd, J=2.8 Hz), 8.07 (1H, d, J=8 Hz.

Preparation 10

3-Cyano-4-iso-propylbenzoic Acid

The title compound was prepared from 4-iso-propylbenzoic acid using a manner similar to that described in Procedures 1 and 5.

$^1$H NMR (DMSO-$D_6$) δ: 1.07 (6H, d, J=7 Hz), 0.13 (1H, m, overlapped), 7.48 (1H, d, J=7 Hz), 7.96(1H, dd. J=2.8 Hz)), 8.00 (1H, d, J=2 Hz).

Preparation 11

4-Methoxy-3-trifluoromethylbenzoic Acid

The title compound was prepared from 3-bromo-4-methoxybenzoic acid and potassium trifluoroacetate in a manner similar to that of Procedures 3 and 4.

$^1$H NMR (DMSO-$D_6$) δ: 3.78 (3H, s), 7.18 (1H, d, J=9 Hz), 7.90(1H, d, J=2 Hz), 8.00 (1H, dd. J=2.9 Hz), 12.70–13.10 (1H, br, exchangeable)

Preparation 12

4-Methoxy-3-trifluoromethylbenzoyl Chloride

The title compound was prepared from 4-methoxy-3-trifluoromethylbenzoic acid with oxalyl chloride and DMF in chloroform at room temperature [D. Levin. Chem. Br. 1977. 20] followed by evaporation in vacuo.

Preparation 13

Methyl 3-Bromo-4-iso-propoxybenzoate

Methyl 3-bromo-4-hydroxybenzoate (2.5 g, 10.8 mmol) in DMF (35 ml) was treated with potassium carbonate (3.0 g, 21.6 mmol), 2-iodopropane (2.76, 21.6 mmol) and then stirred at 25° C. for 48 h. Work-up with ethyl acetate gave the title compound (3.0 g).

$^1$H NMR (250 MHz, $CDCl_3$) δ: 1.41 (6H, d, J=7 Hz), 3.89 (3H, s), 4.66 (1H, m), 6.90 (1H, d, J=8 Hz), 7.93 (1H, dd. J=8.2 Hz), 8.22 (1H, d, J=2 Hz)

Preparation 14

Methyl 3-Cyano-4-iso-propoxybenzoate

Methyl 3-bromo-4-iso-propoxybenzoate (2.0 g, 7.3 mmol) and copper(I)cyanide in N-methyl pyrrolidone (50 ml) was heated under vigorous reflux for 4 h. Work-up with ethyl acetate gave the title compound (1.0 g).

$^1$H NMR (250 MHz. $CDCl_3$) δ: 1.56 (6H, d, J=7 Hz), 4.05 (3H, s), 4.88 (1H, m), 7.13 (1H, d, J=8 Hz), 8.31 (1H, dd. J=8.2 Hz), 8.31 (1H, d. J=2 Hz)

Preparation 15

Methyl 3,5 Dichloro-4-ethoxybenzoate

The title compound was prepared in 69% yield from methyl 3,5-dichloro-4-hydroxybenzoic acid and iodoethane in a manner similar to that of Preparation 6.

$^1$H NMR (250 MHz, $CDCl_3$) δ: 1.47 (3H, t, J=7 Hz), 3.91 (3H, s), 4.16 (2H, q, J=7 Hz), 7.96 (2H, s).

Preparation 16

3-Methanesulfonyl-4-iso-propylbenzoic Acid

3-Chlorosulfonyl-4-iso-propylbenzoic acid (2.62 g, 10 mmol) [made from 4-iso-propyl benzoic acid in a manner similar to that described in Procedures 7 and 8] was added slowly to a slurry of $NaHCO_3$ (2.52 g, 30 mmol) and $Na_2SO_3$ (1.26 g 10 mmol) in water (9 ml) at 75° C. The mixture was stirred for 1 h and then treated with bromoacetic acid (2.08 g, 15 mmol) and NaOH (0.60 g, 15 mmol). The temperature was raised to 105° C. and the mixture heated at reflux for 24 h. The mixture was cooled, acidified to pH 1 and the resultant precipitate collected, washed and dried to give the title compound (1.43 g, 59%).

$^1$H NMR (250 MHz. acetone-D$_6$) δ: 1.24 (6H, d, J=7 Hz), 3.13 (3H, s), 3.88 (1H, m), 7.72 (1H, d, J=7 Hz), 8.15(1H, dd, J=7 Hz), 8.52(1H, d, J=7 Hz).

Preparation 17

3-Chloro-4-ethoxybenzoic Acid $^1$H NMR (DMSO-D$_6$) δ: 1.39 (3H, t, J=7 Hz), 4.20 (2H, q, J=7 Hz), 7.22 (1H, d, J=7 Hz), 7.87 (2H, m).

Preparation 18

3-Bromo-4-iso-propoxybenzoic Acid

The title compound was prepared using a method similar to that of Preparation 7.

$^1$H NMR (DMSO-D$_6$) δ: 1.29 (6H, d, J=7 Hz), 4.77 (1H, sep, J=7 Hz), 7.20 (1H, d, J=8 Hz), 7.87(1H, dd, J=8.2 Hz), 8.02(1H, d, J=2 Hz), 12.92(1H, brs).

Procedure 1

5-Bromo-2,4-dimethoxybenzoic Acid

To a solution of 2.4-dimethoxybenzoic acid (4.0 g. 0.022 mol) in chloroform (60 ml) was added bromine (1.13 ml. 0.022 mol) in chloroform (20 ml) dropwise. After stirring overnight at room temperature the precipitate was filtered off and dried to afford the title compound as a white solid (2.87 g).

Procedure 2

5-Bromo-4-iso-propyl-2-methoxybenzoic Acid

To a solution of 2-methoxy-4-iso-propyl benzoic acid (7.0 g. 36.0 mmol) in chloroform (100 ml) was added bromine (1.86 ml) in chloroform (20 ml) dropwise. The reaction was stirred at room temperature overnight. Evaporation in vacuo afforded an oil (9.27 g).

$^m/_z$ (Cl): 275, 273 (MH$^-$: 70%).

Procedure 3

Methyl-5-bromo-4-iso-propyl-2-methoxy Benzoate

5-Bromo4-iso-propyl-2-methoxybenzoic acid (9.268 g 34.0 mmol) was dissolved in ethanol (250 ml) and conc. H$_2$SO$_4$ (2 ml) added. The mixture was refluxed for 5 h and concentrated in vacuo. Residual material was taken up into ethyl acetate and water, and the organic layer, dried (MgSO$_4$) Concentration in vacuo afforded an oil, which was purified by Biotage Column Chromatography on silica gel using 10% ether in hexane to give an oil (5.5 g).

Procedure 4

2,4-Dimethoxy-5-trifluoromethylbenzoic Acid 2.4-Dimethoxy-5-bromobenzoic acid methyl ester (1.5 g; 5.4 mmol) in DMF (25 ml) and toluene (8 ml) under argon was treated with potassium trifluoroacetate (1.53 g, 10.1 mmol) and copper (I) iodide (2.1 g. 10.9 mmol). The mixture was heated to 170° C. with removal of water (Dean/Stark), and then at 155° C. overnight. The mixture was allowed to cool, poured into ether and water and filtered through Kieselguhr. The organic layer was dried (Na$_2$SO$_4$) and concentrated in vacuo to give a brown solid. Chromatography on Kieselgel 60 with 1:1 ether/petrol gave a solid (1.03 g) which was hydrolysed in 1:1 methanolic: aqueous NaOH (50 ml) at 50° C. Work-up gave the title compound as a white solid (1 g).

Procedure 5a

Methyl 2-methoxy-5-cyano-4-iso-propylbenzoate

Copper (I) cyanide (550 mg, 6 mmol) was added to a solution of methyl 2-methoxy-5-bromo-4-iso-propylbenzoate (861 mg) in N-methyl-2-pyrolidinone (30 ml). The mixture was stirred under argon and boiled under reflux for 4 h. The mixture was cooled, poured into excess ice/water and ethyl acetate and filtered. The organic phase was separated, washed with water, brine and dried(MgSO$_4$). Evaporation gave a crude brown solid which was purified by chromatography on silica gel eluting with ethyl acetate/n-hexane (1:4). The product was obtained as a white solid (523 mg).

$^1$H NMR (250 MHz, CDCl$_3$) δ: 1.33 (6H, d, J=7 Hz), 3.38 (1H, sep. J=7 Hz), 3.89 (3H, s), 3.98 (3H, s), 6.91 (1H, s), 8.08 (1H, s): $^m/_z$ (API$^+$): 234 (MH$^+$. 30%).

Procedure 5b

2-Methoxy-5-cyano-4-iso-propylbenzoic Acid

2N NaOH (1.25 ml) was added to a solution of the methyl ester P5a (490 mg) in methanol (10 ml). The solution was stirred overnight at room temperature. The solution was then diluted with water, concentrated in vacuo and washed with ethyl acetate. The aqueous phase was then acidified with 2N HCl and extracted with ethyl acetate. The extract was washed with brine, dried (MgSO$_4$) and evaporated to dryness giving the product as a white solid (418 mg).

$^1$H NMR (250 MHz, CDCl$_3$) δ: 1.35 (6H, d, J=7 Hz), 3.43 (1H, sep. J=7 Hz), 4.14 (3H, s), 7.00 (1H, s), 8.41 (1H, s); $^m/_z$ (API$^+$): 220 (MH$^+$. 100%).

Procedure 6a

Ethyl 2-ethoxy-4-iso-propyl-5-cyanobenzoate

Ethyl 2-ethoxy-4-iso-propyl-5-bromobenzoate (1.2 g, 3.8 mmol) was treated with copper (I) cyanide (682 mg, 7.6 mmol) in N-methyl-2-pyrrolidinone (40 ml) as described in Procedure 5 to give the title compound as an oil (400 mg).

$^1$H NMR (230 MHz, CDCl$_3$) δ: 1.12 (6H, d, J=7 Hz), 1.30 (3H, t, J=7 Hz), 1.84 (3H, t, J=7 Hz), 3.17 (1H, sep. J=7 Hz), 3.99 (2H, q, J=9 Hz), 4.16 (2H, q, J=7 Hz), 6.69 (1H, s), 7.86 (1H, s): $^m/_z$ (API$^+$): 262 (MH$^+$. 100%).

Procedure 6b

2-Ethoxy-4-iso-propyl-5-cyanobenzoic Acid

The ester P6a (370 mg, 1.41 mmol) was dissolved in methanol (5 ml) and over a 24 h period 1N NaOH (2.1 ml, 2.1 mmol) was added. The solution was concentrated under vacuum, diluted with water and washed with ethyl acetate. The aqueous phase was acidified with 2N HCl and extracted with ethyl acetate. The extract was washed with brine, dried (Mg SO$_4$) and evaporated to give the title acid (306 mg).

$^1$H NMR (250 MHz CDCl$_3$) δ: 1.39 (3H, d, J=7 Hz), 1.66 (3H, t, J=7 Hz), 3.47 (1H, sep, J=7 Hz), 4.46 (1H, q, J=7 Hz), 7.03 (1H, s), 8.47 (1H, s): $^m/_z$ (API$^+$): 234 (MH$^+$. 100%).

Procedure 7

4-Ethoxy-2-methoxy-5-methylsulfonylbenzoic Acid

4-Ethoxy-2-methox-5-chlorosulfonyl benzoic acid in a 49% yield, was prepared in 49% yield using the procedure of M. W. Harrold et al. J. Med. Chem. 1989. 32 874. This was used according to the method of R. W. Brown. J. Org. Chem. 1991. 56. 4974, to the title compound in 19% yield.

$^1$H NMR (DMSO-D$_6$) δ: 1.30 (3H, t), 3.10 (3H, s), 3.83 (3H, s), 4.24 (2H, q), 6.73 (1H, s), 8.07 (1H, s).

Procedure 8

4-iso-Propyl-2-methoxy-3-methylsulfonylbenzoic Acid

This was prepared in a similar manner to the procedure of C. Hansch. B. Schmidhalter. F. Reiter. W. Saltonstall J. Org. Chem., 1956. 21, 265 to afford the intermediate 5-chlorosulfonyl-4-isopropyl-2-methoxybenzoic acid which was converted into the title compound using the method of Procedure 7.

$^1$H NMR (DMSO-D$_6$) δ: 1.30 (6H, d), 3.21 (3H, s), 3.80 (1H, m), 3.94 (3H, s), 7.26 (1H, s), 8.19 (1H, s).

Example 1

N-(5,6,7,8-Tetrahydro-6,8,8-trimethyl[1,6] naphthyridin-3-yl)benzamide hydrochloride 3-Amino-5,6,7,8-tetrahydro-6,8,8-trimethyl [1,6] naphthyridine (96 mg, 0.50 mmol) was dissolved in dry THF (5 ml) and the solution treated with benzoyl chloride (70.3 mg; 0.50 mmol). The mixture was stirred at ambient temperature for 2 h then the precipitate collected by filtration, washed with THF, diethyl ether and dried in vacuo (132 mg; 80%).

$^1$H NMR (250 MHz, (CD$_3$)$_2$SO) δ: 1.42 and 1.54 (2×3H, s), 3.02 (3H, brs), 3.65 (2H, brm), 4.40–4.70 (2H, brm), 7.60–7.71 (3H, m), 8.00–8.10 (2H, m), 8.18 (1H, brs), 8.91 (1H, brs), 10.60–10.90 (2H, brm, exchangeable); $^m/_z$ (API$^+$): 296.1 (MH+).

Example 2

N-(5,6,7,8-Tetrahydro-6,8,8-trimethyl[1,6] naphthyridin-3-yl)-3-cyano-4-iso-propylbenzamide Hydrochloride Prepared in a manner similar to that of Example 1, from 3-cyano-4-iso-propylbenzoic acid as a white powder (171 mg, 86%).

$^1$H NMR (250 MHz, (CD$_3$)$_2$SO) δ: 1.30 (6H, d, J=7 Hz), 1.33 and 1.46 (2×3H, s), 2.94 (3H, d, J=4 Hz), 3.20–3.70 (3H, brm), 4.30–4.60 (2H, m), 7.73 (1H, d, J=8 Hz), 8.09 (1H, d, J=2 Hz), 8.24(1H, dd. J=10.2 Hz), 8.40(1H, d, J=2 Hz), 8.83 (1H, d, J=2 Hz); $^m/_z$ (API$^+$): 363.2 (MH+).

Example 3

N-(5,6,7,8-Tetrahydro-6,8,8-trimethyl[1,6] naphthyridin-3-yl)-4-methoxy-3-trifluoromethylbenzamide hydrochloride Prepared in a manner similar to that of Example 1 from 4-methoxy-3-trifluoromethyl-benzoic acid. The product was purified by chromatography on SiO$_2$, eluting with 0.88 aq. ammonia/methanol/dichloromethane (0.5:4.5:95), and converted into the hydrochloride salt by addition of 1M hydrogen chloride in diethyl ether (1 equivalent). The title compound was collected by filtration (98 mg; 46%).

$^1$H NMR (250 MHz: (CD$_3$)$_2$SO) δ: 1.6 and 1.48 (2×3H, s), 2.96 (3H, d, J=3 Hz), 3.40 and 3.70 (2×1H, brm), 3.99 (3H, s), 4.30–4.60 (2H, br), 7.46 (1H, d, J=9 Hz), 8.10 (1H, d. J=2 Hz), 8.28 (1H, brs), 8.34 (1H, br dd), 8.85 (1H, d, J=2 Hz), 10.60–10.80 (2H, br, exchangeable): $^m/_z$ (API$^+$): 394.2 (MH+).

Example 4

N-(5,6,7,8-Tetrahydro-6,8,8-trimethyl[1,6] naphthyridin-3-yl)-3-bromo-4-ethylbenzamide hydrochloride Prepared in a similar manner to that of Example 3 from 3-bromo-4-ethylbenzoic acid and isolated as an off-white powder (104 mg; 46%).

$^1$H NMR (250 MHz; (CD$_3$)$_2$SO) δ: 1.25 (3H, t, J=7 Hz), 1.40 and 1.54 (2×3H, s), 2.83 (2H, q, J=7 Hz), 3.00 (3H, d, J=4 Hz), 3.30–3.80 (2H, brm) 4.30–4.70 (2H, m), 7.59 (1H, d, J=8 Hz), 8.02 (1H, d, J=8 Hz), 8.16 (1H, d, J=2 Hz), 8.26 (1H, d, J=1 Hz), 8.90 (1H, d, J=2 Hz): $^m/_z$ (API+): 402.1, 404.1 (MH+).

Example 5

N-(5,6,7,8-Tetrahydro-6,8,8-trimethyl[1,6 naphthyridin-3-yl)-3-bromo-4-ethoxybenzamide hydrochloride Prepared in a similar manner to that of Example 3 from 3-bromo-4-ethoxybenzoic acid and isolated as an off-white powder (100 mg: 44%).

$^1$H NMR (250 MHz: (CD$_3$)$_2$SO) δ: 1.42 and 1.55 (2×3H, s), 1.46 (3H, t, J=7 Hz), 3.01 (3H, brd), 3.30–3.80 (2H, m), 4.29 (2H, q, J=2 Hz), 4.30–4.70 (2H, brm), 7.33 (1H, d, J=9 Hz), 8.10 (1H, dd. J=9.2 Hz), 8.16 (1H, d, J=2 Hz), 8.33 (1H, d, J=2 Hz), 8.91 (1H, d, J=2 Hz), 10.64 (1H, s, exchangeable), 10.86 (1H, br, exchangeable).

$^m/_z$ (API$^+$): 418.1, 420.1 (MH+).

Example 6

N-(5,6,7,8-Tetrahydro-6,8,8-trimethyl[1,6] naphthyridin-3-yl)-3-chloro-4-iso-propyloxybenzamide hydrochloride Prepared in a manner similar to that of Example 3 from 3-chloro-4-iso-propyloxybenzoic acid and isolated as an off-white powder (67 mg; 32%).

$^1$H NMR (250 MHz (CD$_3$)$_2$SO) δ: 1.17 (6H, d, J=6 Hz), 1.22 and 1.50 (2×3H, s), 2.78 (3H, brs), 3.40 (2H, brs), 4.20–4.60 (2H, brm), 4.63–4.73 (1H, m), 7.18 (1H, d, J=9 Hz), 7.85(1H, dd, J=9.2 Hz), 7.97 (1H, d, J=2 Hz), 8.04(1H, d, J=Hz), 8.75 (1H, d J=2 Hz); $^m/_z$ (API$^+$): 388.2, 390.2 (MH+).

Example 7

N-(5,6,7,8-Tetrahydro-6,8,8-trimethyl[1,6] naphthyridin-3-yl)-3-bromo-4-iso-propyloxybenzamide hydrochloride Prepared in a manner similar to that of Example 3 from 3-bromo-4-iso-propyloxybenzoic acid and isolated as an off-white powder (224 mg: 82%).

$^1$H NMR (250 MHz: (CD$_3$)$_2$SO) δ: 1.24 (6H, d, J=6 Hz), 1.26 and 1.35 (2×3H, s). 2.89 (3H, brd), 3.30(2H, brm), 4.20–4.50 (2H, brm), 4.74(1H, m), 7.20 (1H, d, J=9 Hz), 7.90 (1H, dd, J=9.2 Hz), 7.92 (1H, d, J=2 Hz), 8.15 (1H, d, J=2 Hz), 8.72 (1H, d, J=2 Hz): $m/z$ (API$^+$): 434, 432 (MH+; 80%).

Example 8

N-(5,6,7,8-Tetrahydro-6,8,8-trimethyl[1,6]naphtlyridin-3-yl)-3-acetyl-4-isopropyloxybenzamide hydrochloride Prepared as described in Example 3 from 3-acetyl-4-isopropyloxybenzoic acid (222 mg: 1.0 mmol), except that the reaction was performed in dichloromethane and in the presence of triethylamine (101 mg; 1.0 mmol; 0.14 ml). The title compound was isolated as a white powder (247 mg; 57%).

$^1$H NMR [free base] (250 MHz: CD$_3$OD) δ: 1.22 (6H, s), 1.32 (6H, d, J=6 Hz), 2.31 (3H, s), 2.44 (2H, s), 2.50(3H, s), 3.45(21H, s), 4.77(1H, m), 7.12 (1H, d, J=9 Hz), 7.79 (1H, d, J=2 Hz), 7.95 and 7.99 (1H, dd, J=9, 2 Hz), 8.16 (1H, d, J=2 Hz), 8.56 (1H, d, J=2 Hz); $m/z$ (API)$^+$: 396.2 (MH+; 80%).

Example 9

N-(5,6,7,8-Tetrahydro-6,8,8-trimethyl[1,6]naphthyridin-3-yl)-4-ethoxy-3-trifluoromeethylbenzamide dihydrochloride Prepared as described in Example 8 from 4-ethoxy-3-trifluoromethylbenzoic acid (237 mg; 1.0 mmol) and isolated as a white powder (416 mg; 87%).

$^1$H NMR [free base] (250 MHz: CD$_3$OD) δ: 1.23 (6H, s), 1.34 (3H, t, J=7 Hz), 2.32 (3H, s), 2.45 (2H, s), 3.46(2H, s), 4.13 (2H, q, J=7 Hz), 7.16(1H, d, J=9 Hz), 7.80 (1H, d, J=2 Hz), 8.09 (2H, m), 8.57 (1H, d, J=2 Hz); $m/z$ (API)$^+$: 408.2 (MH+; 80%,

Example 10

N-(8,8-Dimethyl-5,6,7,8-tetrahydro[1,6]naphthyridin-3-yl)-4-methoxy-3-trifluoromethylbenzamide hydrochloride N-(5,6,7,8-Tetrahydro-6,8,8-trimethyl[1,6]naphthyridin-3-yl)-4-methoxy-3-trifluoromethylbenzamide (172 mg; 0.44 mmol) was suspended in 1.2-dichloromethane (30 ml) and the mixture treated with 1-chloroethyl chloroformate (62.5 mg; 47 ml; 0.44 mmol). The mixture was heated at reflux and more chloroformate added until little or no starting material remained. At this point, the volatiles were removed under reduced pressure and the residue dissolved in methanol (30 ml) and heated at reflux for 15 min. The volatiles were removed under reduced pressure and the residue treated with a mixture of 0.88 aqueous ammonia/methanol/dichloromethane (0.5:4.5:95) and the resulting, beige solid was collected by filtration. The free base (123 mg; 0.32 mmol) was dissolved in methanol (min. vol) and treated with IM hydrogen chloride in diethyl ether (0.32 ml; 0.32 mmol) and the mixture diluted with diethyl ether to turbidity and refrigerated. The title compound was obtained as white powder (130 mg; 71%).

$^1$H NMR [free base] (250 MHz; CD$_3$OD) δ: 1.37 (6H, s), 3.35 (2H, s), 4.35 (2H, s), 7.25 (1H, d, J=9 Hz), 3.07 (1H, d, J=2 Hz), 8.15–8.18 (2H, m), 8.70 (1H, d, J=2 Hz); m/z (API)$^+$: 373.1 (MH+; 100%).

The following examples were prepared using methods described above:

Example 11

N-(5,6,7,8-Tetrahydro-6,8,8-trimethyl[1,6]naphthyridin-3-yl)-3-bromo-4-methoxybenzamide hydrochloride $^1$H NMR [free base] (250 MHz; CD$_3$OD) δ: 1.04 (6H, s), 2.13 (3H, s), 2.26 (2H, s), 3.27 (2H, s), 3.65 (3H, s), 6.84 (1H, d, J=9 Hz), 7.59 (1H, d, J=2 Hz), 7.66(1H, dd, J=9.2 Hz), 7.88 (1H, d, J=2 Hz), 8.37 (1H, d, J=2 Hz): m/z (API)$^+$: 425.7, 428 (M+Na+).

Example 12

N-(5,6,7,8-Tetrahydro-6,8,8-trimethyl[1,6]naphthyridin-3-yl)-3-chloro-4-methoxybenzamide hydrochloride $^1$H NMR [free base] (250 MHz; CD$_3$OD) δ1.41 (6H, s), 2.50 (3H, s), 2.64 (2H, s), 3.56 (2H, s), 4.03 (3H, s), 7.26(1H, d, J=9 Hz), 7.97–8.09 (3H, m), 8.73 (1H, d, J=2 Hz); m/z (API)$^+$: 382.1, 384.2 (M+Na)$^+$.

Example 13

N-(5,6,7,8-Tetrahydro-6,8,8-trimethyl[1,6]naphthyridin-3-yl)-3-cyano-4-methoxybenzamide hydrochloride $^1$H NMR [free base] (250 MHz; CD$_3$OD) δ: 1.33 (6H, s), 2.43 (3H, s), 2.56 (2H, s), 3.58 (2H, s), 4.03 (3H, s), 7.31 (1H, d, J=9 Hz), 7.90(1H, d, J=2 Hz), 8.23 (2H, m), 8.66 (1H, d, J=2 Hz): m/z (API)$^+$: 351.1 (MH$^+$. 80%), 373.2 (M+Na)$^+$.

Example 14

N-(5,6,7,8-Tetrahydo-6,8,8-trimethyl[1,6]naphthyridin-3-yl)-3-cyano-4-ethylbenzamide hydrochloride $^1$H NMR [free base] (250 MHz; CD$_3$OD) δ: 1.10 (9H, m), 2.20 (3H, s), 2.34 (2H, s), 2.71 (2H, q, J=8 Hz), 3.36 (2H, s), 7.37 (1H, d, J=8 Hz),7.70(1H, d, J=2 Hz), 7.93 (1H, dd, J=8.2 Hz), 8.04(1H, d J=2 Hz), 8.45 (1H, d, J=2 Hz): m/z(API)$^+$: 349 (MH+).

Example 15

N-(5,6,7,8-Tetrahydro-6,8,8-trimethyl[1,6]naphthyridin-3-yl)-3-bromo-4-methylbenzamide hydrochloride $^1$H NMR [free base] (250 MHz; CD$_3$OD) δ6: 1.23 (6H, s), 2.32, 2.33 (2×3H, s), 2.45 (2H, s), 3.44 (2H, s), 7.30 (1H, d, J=8 Hz), 7.72 (1H, dd, J=8.2 Hz), 7.79 (1H, d, J=2), 8.02 (1H, d, J=2 Hz), 8.56 (1H, d, J=2 Hz): m/z (API$^-$):386.0, 387.9 (M–H)$^-$.

Example 16

N-(5,6,7,8-Tetrahydro-6,8,8-trimethyl[1,6]naphthyridin-3-yl)-3-pivaloylbenzamide $^1$H NMR (250 MHz; CDCl$_3$) δ: 1.36 (6H, s), 1.38 (9H, s), 2.45 (3H,s), 2.52 (2H, s), 3.59 (2H, s), 7.55 (1H, t, J=8 Hz), 7.88 (1H, m), 7.97 (2H, m), 8.17 (1H, s), 8.44 (1H, d, J=2 Hz); m/z (API$^+$): 380.4 (MH$^+$: 30%).

Example 17

N-(5,6,7,8-Tetrahydro-6,8,8-trimethyl[1,6]naphthyridin-3-yl)-5-chloro-2-methoxy-4-isopropyloxybenzamide hydrochloride $^1$H NMR [free base] (250 MHz; CDCl$_3$) δS: 1.35 (6H, s), 1.44 (6H, d, J=6 Hz), 2.44 (3H, s), 2.51 (2H, s), 3.37 (2H, s), 4.05 (3H, s), 4.66 (1H, m), 6.57 (1H, s), 8.06 (1H, d, J=2 Hz), 8.26 (1H, s), 8.34 (1H, d, J=2 Hz); m/z (API$^+$): 416.1, 418.2 (M+H])$^+$.

Example 18

N-(5,6,7,8-Tetrahydro-6,8,8-trimethyl[1,6] naphthyridin-3-yl)-3-cyano-4-ethoxybenzamide hydrochloride $^1$H NMR [free base] (250 MHz; CD$_3$OD) δ: 1.27 (6H, s), 1.42 (3H, t, J=7 Hz), 2.37 (3H, s), 0.50 (2H, s), 3.52 (2H, s) 4.22 (2H, q, J=7 Hz), 7.22 (1H, d, J=9 Hz), 7.84 (1H, d, J=2 Hz), 8.16 (2H, m), 8.60 (1H, d, J=2 Hz): m/z (API$^+$): 365.1 (M+H)$^+$.

Example 19

N-(5,6,7,8-Tetrahydro-6,8,8-trimethyl[1,6] naphthyridin-3-yl)-4-methoxy-3-trifluoroacetylbenzamide $^1$H NMR (250 MHz; CDCl$_3$) δ: 1.34 (6H, s), 2.44 (3H, s), 2.51 (2H, s), 3.55 (2H, s), 3.99 (3H, s), 7.10(1H, d, J=8 Hz), 7.93 (1H, d, J=8 Hz), 8.23 (2H, brm), 8.44 (1H, brs), 8.51 (1H, d, J=2 Hz); m/z (API$^+$): 422.1 (MH$^+$; 100%).

Example 20

N-(5,6,7,8-Tetrahydro-6,8,8-trimethyl[1,6]naphthyridin-3-yl)naphthalene-2-carboxamide $^1$H NMR (250 MHz; CDCl$_3$) δ: 1.42 (6H, s), 2.61 (3H, s), 2.76 (2H, s), 3.78 (2H, s), 7.20 (1H, m), 7.50–8.65 (7H, m), 7.95 (1H, d, J=2 Hz), 8.46 (1H, s), 8.72 (1H, d, J=2 Hz); m/z (API$^+$): 346.1 (MH$^+$: 70%).

Example 21

N-(5,6,7,8-Tetrahydro-6,8,8-trimethyl[1,6] naphthyridin-3-yl)-3-cyano-4-iso-propyloxybenzamide hydrochloride $^1$H NMR[free base] (250 MHz:CD$_3$OD) δ: 1.24 (6H, s), 1.32 (6H, d, J=6 Hz), 2.34 (3H, s), 2.48 (2H, s), 3.49 (2H, s), 4.74–4.84 (1H, m), 7.21 (1H, d, J=9 Hz), 7.81 (1H, d, J=2 Hz), 8.10 (1H, dd, J=9.2 Hz), 8.14 (1H, d, J=2 Hz), 8.57(1H, d, J=2 Hz); m/z (API$^+$): 379.2 (MH$^+$)

Example 22

N-(5,6,7,8-Tetrahydro-6,8,8-trimethyl[1,6] naphthyridin-3-yl)-3-acetyl-4-ethylbenzamide hydrochloride $^1$H NMR [free base] (250 MHz; CD$_3$OD) δ: 0.98 (3H, t, J=7 Hz), 1.11 (6H, s), 2.20 (3H, s), 2.34 (2H, s), 2.41 (3H, s), 2.67 (2H, q, J=7 Hz), 3.34 (2H, s), 7.22 (1H, brd, J=8 Hz), 7.70 (1H, brs), 7.78 (1H, brd, J=8 Hz), 8.08 (1H, brs), 8.47 (1h, brs); m/z (API$^+$): 366.2 (MH$^+$)

Example 23

N-(5,6,7,8-Tetrahydro-6,8,8-trimethyl[1,6] naphthyridin-3-yl)-2,3-dihydrobenzofuran-5-carboxamide hydrochloride 1H NMR [free base] (250 MHz;CD$_3$OD) δ: 1.35 (6H, s) 2.44(3H, s), 2.58 (2H, s), 3.26 (2H, t, J=9 Hz), 3.58(2H, s), 4.64 (2H, t, J=9 Hz), 6.81 (1H, d, J=8 Hz), 7.76 (1H, dd, J=8.2 Hz), 7.83 (1H, brs), 7.89 (1H, d, J=2 Hz), 8.67(1H, d, J=2 Hz): m/z (API$^+$): 338.2 (MH$^+$)

Example 24

N-(5,6,7,8-Tetrahydro-6,8,8-trimethyl[1,6] naphthyridin-3-yl)-3-n-butyroyl-4-methoxybenzamide hydrochloride $^1$H NMR [free base] (250 MHz; CD$_3$OD) δ: 0.71 (3H, t, J=7 Hz), 1.08(6H, s), 1.42 (2H, m), 2.17(3H, s), 2.31 (2H, s), 2.72 (2H, t, J=7 Hz), 3.32 (2H, s), 3.74 (3H, s); 7.00 (1H, d, J=9 Hz), 7.64 (1H, m), 7.86(1H, dd, J=9.2 Hz), 7.95 (1H, d, J=2 Hz), 8.41 (1H, d, J=2 Hz), m/z (API$^+$): 396.2 (MH$^+$), 418.2 (M+Na$^+$).

Example 25

N-(5,6,7,8-Tetrahydro-6,8,8-trimethyl[1,6] naphthyridin-3-yl)-4-methoxy-3-n-propionylbenzamide hydrochloride $^1$H NMR [free base] (250 MHz; CD$_3$OD) δ: 1.12 (3H, t, J=7 Hz), 1.31 (6H, s), 2.41 (3H, s), 2.54 (2H, s), 3.00 (2H, q, J=7 Hz), 3.56 (2H, s), 3.97 (3H, s), 7.24 (1H, d, J=9 Hz), 7.88 (1H, d, J=2 Hz) 8.10(1H, dd, J=9.2 Hz), 8.21(1H, d, J=2 Hz), 8.64(1H, d, J=2 Hz); m/z (API$^+$): 382.2 (MH$^+$).

Example 26

N-(5,6,7,8-Tetrahydro-6,8,8-trimethyl[1,6] naphthyridin-3-yl-iso-butyroyl-4-methoxybenzamide hydrochloride $^1$H NMR [free base] (250 MHz;CD$_3$OD)δ:1.04 (6H, d, 7 Hz), 1.25 (6H, s), 2.36 (3H, s) 2.76 (2H, s), 3.40 (1H, m), 3.51 (2H, s), 3.88 (3H, s), 7.15 (1H, d, J=8 Hz), 7.82 (1H, d, J=2 Hz), 8.02 (2H, m), 8.58 (1H, d, J=2 Hz); m/z (API$^+$): 396.3 (MH$^+$).

Example 27

N-(8,8-Dimethyl-5,6,7,8-tetrahydro[1,6] naphthyridin-3-yl)-4-ethoxy-3-trifluoromethylbenzamide hydrochloride $^1$H NMR [HCl salt] (250 MHz;CD$_3$OD) δ:1.53 (3H, t, J=7 Hz), 1.69(6H, s), 3.64 (2H, s), 4.35 (2H, q, J=7 Hz), 4.71 (2H, s), 7.41 (1H, d, J=9 Hz), 8.38 (2H, m), 8.70 (1H, d, J=2 Hz), 9.38 (1H, d, J=2 Hz); m/z (API$^-$): 364 1 [M–Et].

Example 28

N-(8,8-Dimethyl-5,6,7,8-tetrahydro[1,6] naphthyridin-3-yl)-3-acetyl-4-iso-propyloxybenzamide hydrochloride $^1$H NMR [free base] (250 MHz; CD$_3$OD) δ: 1.22 (6H, s), 1.34 (6H, d, J=6 Hz), 2.53 (3H, s), 2.84 (2H, s), 3.78 (2H, s), 4.76–4.86 (1H, m), 7.15 (1H, d, J=9 Hz). 7.79 (1H, d, J=2 Hz), 7.99 (1H, dd, J=9.2 Hz), 8.18 (1H, d, J=2 Hz), 8.57(1H, d, J=Hz); m/z (API$^+$): 382.2 (MH$^+$).

Example 29

N-(8,8-Dimethyl-5,6,7,8-tetrahydro[1,6] naphthyridin-3-yl)-3-bromo-4-methoxybenzamide hydrochloride $^1$H NMR [HCl salt] (250 MHz;(CD$_3$)$_2$SO)δ: 1.27 (6H, s), 3.19 (2H, brs), 3.81 (3H, s), 4.22 (2H, brs), 7.14 (1H, d, J=9 Hz), 7.94(1H, brdd), 8.08(1H, brd), 8.14 (1H, d, J=2 Hz), 8.73 (1H, brd), 9.45–9.70 (2H, brs, exchangeable), 10.53 (1H, brs, exchangeable); m/z (API$^-$): 389.8, 387.9 (M–H).

Example 30

N-(8,8-Dimethyl-5,6,7,8-tetrahydro [1,6] naphthyridin-3-yl)-3-chloro-4-methoxybenzamide hydrochloride $^1$H NMR [HCl salt] (250 MHz: (CD$_3$)$_2$SO) δ: 1.40 (6H, s), 3.30 (2H, brs), 3.91 (3H, s), 4.33 (2H, brs), 7.28(1H, d, J=8 Hz), 8.02(1H, dd, J=9.2 Hz), 8.11 (1H, d, J=2 Hz), 8.25 (1H, d, J=2 Hz), 8.88 (1H, d, J=2 Hz), 9.85 (2H, brs, exchangeable), 10.73 (1H, s, exchangeable); m/z (API$^+$): 346.1, 347.2 (MH$^+$: 100%)

Example 31

N-(8,8-Dimethyl-3,6,7,8-tetrahydro[1,6] naphthyridin-3-yl)-4-methoxy-3-pentafluoroethyl benzamide $^1$H NMR (400 MHz; CDCl$_3$) δ: 1.32 (6H, s), 2.96 (2H, s), 3.96 (3H, s), 4.05 (2H, s), 7.13 (1H, d), 7.93 (1H, s), 8.04 (1H, s), 8.06(1H, s), 8.44((1H, d); m/z (API +): 430 (M+H)$^-$

Example 32

N-(8,8-Dimethyl-5,6,7,8-tetrahydro[1,6] naphthyridin-3-yl)-4-iso-propoxy-3-trifluoromethyl benzamide $^1$H NMR (400 MHz; CD$_3$OD) δ: 1.41 (6H, d, J=6 Hz), 1.70 (6H, s), 3.63 (2H, s), 4.71 (2H, s), 4.95 (1H, m—overlapped by solvent), 7.40 (1H, d), 8.32 (1H, s), 8.34 (1H, d), 8.73 (1H, s), 9.45 (1H, s); m/z (API+): 408 (M+H)$^-$

Example 33

N-(8,8-Dimethyl-5,6,7,8-tetrahydro[1,6] naphthyridin-3-yl)-4-ethyl-3-trifluoromethyl benzamide $^1$H NMR (400 MHz; CD$_3$OD) δ: 1.35 (3H, t, J=7 Hz), 1.62 (6H, s), 2.96 (2H, q), 3.57 (2H, s), 4.63 (2H, s), 7.68 (1H, d), 8.25 (1H, d), 8.33 (1H, s), 8.57 (1H, s), 9.21 (1H, s); m/z (API+): 378 (M+H)$^-$

Example 34

N-(8,8-Dimethyl-5,6,7,8-tetrahydro[1,6] naphthyridin-3-yl)-3-bromo-4-iso-propyl benzamide $^1$H NMR (400 MHz; CD$_3$OD) δ: 1.32 (6H, d, J=6 Hz), 1.65 (6H, s), 3.50 (1H, m), 3.59 (2H, s), 4.67 (2H, s), 7.58 (1H, d), 8.02 (1H, d), 8.26 (1H, s), 8.63 (1H, s), 9.32 (1H, s), m/z (API$^+$): 402, 404 (M+H)$^-$

Example 35

N-(5,6,7,8-Tetrahydro-6,8,8-trimethyl[1,6] naphthyridin-3-yl)-3-chloro-4-ethoxybenzamide $^1$H NMR (250 MHz; CDCl$_3$) δ: 1.36 (6H, s), 1.52 (3H, t, J=7 Hz), 2.45 (3H, s), 2.53 (2H, s), 3.59 (2H, s), 4.19(2H, q, J=7 Hz), 7.00(1H, d, J=7 Hz), 7.64(1H, brs), 7.76 (1H, dd, J=7.2 Hz), 7.90 (1H, d, J=2 Hz), 7.98(1H, d, J=2 Hz), 8.42(1H, d, J=2 Hz); m/z (API$^+$): 396.2 (M+Na$^+$, 100%), 374.2 (MH$^+$: 33%).

Example 36

N-(5,6,7,8-Tetrahydro-6,8,8-trimethyl[1,6] naphthyridin-3-yl)-3-fluoro-4-methoxybenzamide $^1$H NMR (400 MHz; CDCl$_3$) δ: 1.35 (6H, s), 2.44 (3H, s), 2.50 (2H, s), 3.56 (2H, s), 3.99 (3H, s), 7.03 (1H, t, J=7 Hz), 7.62 (1H, d), 7.72 (1H, s), 7.95 (1H, d, J=2 Hz), 8.40 (1H, d, J=2 Hz); m/z (API$^+$): 344.2 (MH$^+$; 93%).

Example 37

N-(5,6,7,8-Tetrahydro-6,8,8-trimethyl[1,6] naphthyridin-3-yl)-4-methoxy-3-pentafluoroethylbenzamide $^1$H NMR (400 MHz; CDCl$_3$) δ: 1.35 (6H, s), 2.46 (3H, s), 2.51 (2H, s), 3.57 (2H, s), 3.96 (3H, s), 7.10(1H, d, J=7 Hz), 7.71 (1H, s), 7.93(1H, d, J=2 Hz), 8.04 (1H, d, 8.06 (1H, d), 8.44 (1H, d, J=2 Hz); m/z (API$^+$): 444 (MH$^+$; 90%).

Example 38

N-(8,8-Dimethyl-5,6,7,8-tetrahydro[1,6] naphthyridin-3-yl)-3-fluoro-4-methoxybenzamide hydrochloride $^1$H NMR (250 MHz; CDCl$_3$) [free base] δ: 1.32 (6H, s), 2.20 (2H, s), 3.07 (2H, s), 3.96 (3H, s), 4.04 (2H, s), 7.02 (1H, t, J=7 Hz), 7.62 (1H, d), 7.64 (1H, d), 7.95 (1H, d, J=2 Hz), 8.44 (1H, d, J=2 Hz); m/z (API$^+$): 330 (MH$^+$; 100%).

Example 39

N-(8,8-Dimethyl-5,6,7,8-tetrahydro[1,6] naphthyridin-3-yl)-4-methoxy-3-propionylbenzamide $^1$H NMR (250 MHz; CDCl$_3$) δ: 1.18 (3H, t, J=7 Hz), 1.32 (6H, s), 2.96 (2H, s), 3.05 (2H, q, J=7 Hz), 3.99(3H, s), 4.05(2H, s), 7.11 (1H, d, J=7 Hz), 7.97 (1H, d, J=2 Hz), 8.11 (2H, d), 8.16 (1H, d), 8.45 (1H, d); m/z (API$^+$): 390 (MNa$^+$: 93%), 368 (MH$^+$80%)

Example 40

N-(5,6,7,8-Tetrahydro-6,8,8-trimethyl[1,6] naphthyridin-3-yl)-indole-2-carboxamide $^1$H NMR (250 MHz; CDCl$_3$ +CD$_3$OD) δ: 1.34 (6H, s), 2.46 (3H, s), 2.56 (2H, s), 3.60 (2H, s), 7.20–7.90(6H, m), 8.12(1H, d, J=2 Hz), 8.40 (1H, d, J 2 Hz), 8.60 (1H, brd, J=8 Hz); m/z (API$^+$): 335.2 (MH$^+$: 100%).

Pharmacological Data

1. Binding Assay Method

WO 92/22293 (SmithKline Beecham) discloses compounds having anti-convulsant activity including inter alia the compound trans-(+)-6-acetyl-4S-(4-fluorobenzoylamino)-3,4-dihydro-2,2-dimethyl-2H-1-benzopyran-3R-ol (hereinafter referred to as Compound A). It has been found that the compounds of WO 92/22293 bind to a novel receptor obtainable from rat forebrain tissue, as described in WO 96/18650 (SmithKline Beecham). The affinity of test compounds to the novel receptor site is assessed as follows.

Method

Whole forebrain tissue is obtained from rats. The tissue is first homogenised in buffer (usually 50 mM Tris/HCl, pH 7.4). The homogenised tissue is washed by centrifugation and resuspension in the same buffer, then stored at −70° C. until used.

To carry out the radioligand binding assay, aliquots of tissue prepared as above (usually at a concentration of 1–2 mg protein/ml) are mixed with aliquots of [3H]-Compound A dissolved in buffer. The final concentration of [3H]-Compound A in the mixture is usually 20 nM. The mixture is incubated at room temperature for 1 hour. [3H]-

Compound A bound to the tissue is then separated from unbound [3H]-Compound A by filtration through Whatman GF/B glass fibre filters. The filters are then washed rapidly with ice-cold buffer. The amount of radioactivity bound to the tissue trapped on the filters is measured by addition of liquid scintillation cocktail to the filters followed by counting in a liquid scintillation counter.

In order to determine the amount of "specific" binding of [3H]-Compound A, parallel assays are carried out as above in which [3H]-Compound A and tissue are incubated together in the presence of unlabelled Compound A (usually 3 μM). The amount of binding of [3H]-Compound A remaining in the presence of this unlabelled compound is defined as "non-specific" binding. This amount is subtracted from the total amount of [3H]-Compound A binding (i.e. that present in the absence of unlabelled compound) to obtain the amount of "specific" binding of [3H]-Compound A to the novel site.

The affinity of the binding of test compounds to the novel site can be estimated by incubating together [3]-Compound A and tissue in the presence of a range of concentrations of the compound to be tested. The decrease in the level of specific [3H]-Compound A binding as a result of competition by increasing concentrations of the compound under test is plotted graphically, and non-linear regression analysis of the resultant curve is used to provide an estimate of compound affinity in terms of pKi value.

Results

Compounds of this invention were active in this test with pKi>6. For example, compounds of Examples 2–11 and 25–34 gave pKi values greater than 8.

2. MEST Test

The maximal electroshock seizure (MEST) threshold test in rodents is particularly sensitive for detecting potential anticonvulsant properties[1]. In this model, anticonvulsant agents elevate the threshold to electrically-induced seizures whilst proconvulsants lower the seizure threshold.

Method for Mouse Model

Mice (naive male. Charles River. U.K. CD-1 strain. 25–30 g) are randomly assigned to groups of 10–20 and dosed orally or intraperitoneally at a dose volume of 10 ml/kg with various doses of compound (0.3–300 mg/kg) or vehicle. Mice are then subjected at 30 or 60 min post dose to a single electroshock (0.1 sec. 50 Hz, sine wave form) administered via corneal electrodes. The mean current and standard error required to induce a tonic seizure in 50% ($CC_{50}$) of the mice in a particular treatment group is determined by the 'up and down' method of Dixon and Mood (1948)[2]. Statistical comparisons between vehicle- and drug-treated groups are made using the method of Litchfield and Wilcoxon (1949)[3].

In control animals the $CC_{50}$ is usually 14–18 mA. Hence the first animal in the control group is subjected to a current of 16 mA. If a tonic seizure does not ensue, the current is increased for a subsequent mouse. If a tonic convulsion does occur, then the current is decreased, and so on until all the animals in the group have been tested.

Studies are carried out using a Hugo Sachs Electronik Constant Current Shock Generator with totally variable control of shock level from 0 to 300 mA and steps of 2 mA are usually used.

Method for Rat Model

The threshold for maximal (tonic hindlimb extension) electroshock seizures in male rats (Sprague Dawley. 80–150 g. 6 weeks old) was determined by a Hugo Sachs Electronik stimulator which delivered a constant current (0.3 sec duration; from 1–300 mA in steps of 5–20 mA). The procedure is similar to that outlined above for mouse and full details are as published by Upton et al,.[4]

The percentage increase or decrease in $CC_{50}$ for each group compared to the control is calculated.

Drugs are suspended in 1% methyl cellulose.

Results

At a dosage of 2 mg/kg p.o. at 2 h. the compounds of Examples 3 and 5 showed increases in the rat model of 314% and 350% respectively.

References

1. Loscher, W. and Schmidt, D. (1988). Epilepsy Res. 2. 145–181
2. Dixon, W. J. and Mood, A. M. (1948). J. Amer. Stat. Assn. 43, 109–126
3. Litchfield, J. T. and Wilcoxon, F. (1949). J. Pharmacol. exp. Ther. 96. 99–113
4. N. Upton, T. P. Blackburn, C. A. Campbell, D. Cooper, M. L. Evans, H. J. Herdon, P. D. King, A. M. Ray, T. O. Stean, W. N. Chan, J. M. Evans and M. Thompson, (1997). B. J. Pharmacol., 121. 1679–1686

What is claimed is:

1. A compound of formula (I) or a pharmaceutically acceptable salt or solvate thereof:

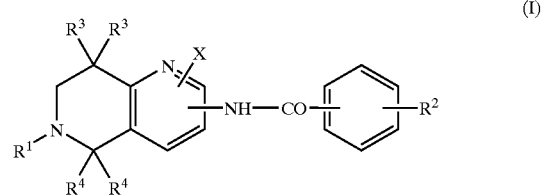

(I)

where $R^1$ is hydrogen, $C_{1-6}$alkyl (optionally substituted by hydroxy or $C_{1-4}$alkoxy), phenyl-$C_{1-4}$alkyl-, $C_{2-6}$alkenyl, or $C_{2-6}$alkynyl;

$R^2$ is hydrogen or up to three substituents selected from halogen, $NO_2$, $CN$, $N_3$, $CF_3O$—, $CF_3S$—, $CF_3SO_2$—, $CF_3CO$—, $C_{1-6}$alkyl, $C_{2-6}$alkenyl, $C_{2-6}$alkynyl, $C_{1-6}$perfluoroalkyl, $C_{3-6}$cycloalkyl, $C_{3-6}$cycloalkyl-$C_{1-4}$alkyl-, $C_{1-6}$alkylO—, $C_{1-6}$alkylCO—, $C_{3-6}$cycloalkylO—, $C_{3-6}$cycloalkylCO—, $C_{3-6}$cycloalkyl-$C_{1-4}$alkylO—, $C_{3-6}$cycloalkyl-$C_{1-4}$alkylCO—, phenyl, phenoxy, benzyloxy, benzoyl, phenyl-$C_{1-4}$alkyl-, $C_{1-6}$alkylS—, $C_{1-6}$alkylSO_2$—, $(C_{1-4}$alkyl$)_2$NSO_2$—, $(C_{1-4}$alkyl$)$NHSO_2$—, $(C_{1-4}$alkyl$)_2$NCO—, $(C_{1-4}$alkyl$)$NHCO— or $CONH_2$;

or —$NR^5R^6$ where $R^5$ is hydrogen or $C_{1-4}$ alkyl, and $R^6$ is hydrogen, $C_{1-4}$alkyl, formyl, —$CO_2C_{1-4}$alkyl or —$COC_{1-4}$alkyl;

or two $R^2$ groups together form a carbocyclic ring that is saturated or unsaturated, optionally interrupted by O or NH;

$R^3$ groups and $R^4$ groups are each independently hydrogen or $C_{1-6}$ alkyl and/or the two $R^3$ groups and/or the two $R^4$ groups together form a $C_{3-6}$ spiroalkyl group, provided that at least one $R^3$ or $R^4$ group is not hydrogen; and X is selected from hydrogen, halogen, cyano, alkyl and alkoxy.

2. A compound according to claim 1 of formula (IA)

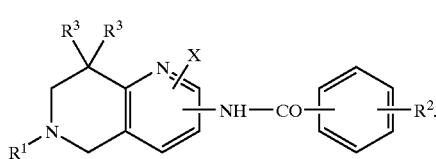

3. A process for the preparation of compounds according to claim 1 which comprises racting a compound of formula (II):

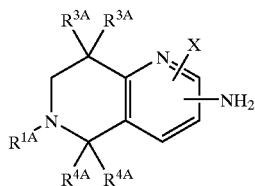

where $R^{1A}$, $R^{3A}$, $R^{4A}$, X are $R^1$, $R^3$, $R^4$, X as defined for formula (I) or a group or groups convertible to $R^1$, $R^3$, $R^4$, X with a compound of formula (III):

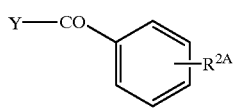

where Y is a leaving group, and $R^{2A}$ groups are independently $R^2$ as defined for formula (I) or a group or groups convertible to $R^2$, and where required converting an $R^{1A}$, $R^{2A}$, $R^{3A}$, $R^{4A}$, X group to a $R^1$, $R^2$, $R^3$, $R^4$, X group, converting one $R^1$, $R^2$, $R^3$, $R^4$, X group to another $R^1$, $R^2$, $R^3$, $R^4$, X group, or converting a salt product to the free base or another pharmaceutically acceptable salt, or separating any enantiomers, or converting a free base product to a pharmaceutically acceptable salt.

4. A compound according to claim 1 for formula (IB):

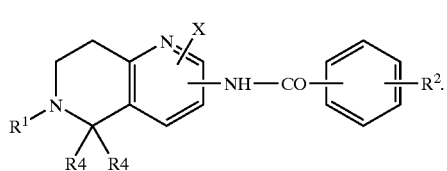

5. A pharmaceutical composition for use in the treatment and/or prophylaxis of anxiety, mania, depression, panic disorders and/or aggression, disorders associated with a subarachnoid haemorrhage or neurl shock, the effects associated with withdrawal from substances of abuse, epilepsy, post-traumatic epilepsy, Parkinson's disease, psychosis, migraine, cerebral ischaemia, Alzheimer's disease, Huntingdon's chorea, schizophrenia, obsessive compulsive disorders, neurological deficits associated with AIDS, sleep disorders, circadian rhythm disorders, insomnia, narcolepsy, tics, Giles de la Tourette's syndrome, traumatic brain injury, tinnitus, neuralgia, trigeminal neuralgia, neuropathic pain, dental pain, cancer pain, diabetes, multiple sclerosis and motor neurone disease, ataxias, muscular rigidity, temporomandibular joint dysfunction, and amyotrophic lateral sclerosis which comprises a compound according to claim 1 and a pharmaceutically acceptable carrier.

6. A method of treatment and/or prophylaxis of anxiety, mania, depression, panic disorders and/or aggression, disorders associated with a subarachnoid haemorrhage or neural shock, the effects associated with withdrawal from substances of abuse, epilepsy, post-traumatic epilepsy, Parkinson's disease, psychosis, migraine, cerebral iscbaemia, Alzheimer's disease, Huntingdon's chorea, schizophrenia, obsessive compulsive disorders, neurological deficits associated with AIDS, sleep disorders, circadian rhythm disorders, insomnia, narcolepsy, tics, Giles de la Tourette's syndrome, traumatic brain injury, tinnitus, neuralgia, trigeminal neuralgia, neuropathic pain, dental pain, cancer pain, diabetes, multiple sclerosis and motor neurone disease, ataxias, muscular rigidity, temporomandibular joint dysfunction, and amyotrophic lateral sclerosis comprising administering to the sufferer in need thereof an effective or prophylactic amount of a compound according to claim 1.

* * * * *